(12) United States Patent
Sviridov et al.

(10) Patent No.: US 8,030,488 B2
(45) Date of Patent: Oct. 4, 2011

(54) PIPERAZINE DERIVATIVES AS STEAROYL-COA DESATURASE INHIBITORS AND THEIR USE AS THERAPEUTIC AGENTS

(75) Inventors: Serguei Sviridov, Burnaby (CA); Vishnumurthy Kodumuru, Burnaby (CA); Shifeng Liu, Port Coquitlam (CA); Melwyn Abreo, Jamul (CA); Michael D. Winther, Vancouver (CA); Heinz W. Gschwend, Santa Rosa (CA); Rajender Kamboj, Burnaby (CA); Shaoyi Sun, Vancouver (CA); Mark W. Holladay, San Diego, CA (US); Wenbao Li, San Diego, CA (US); Chi Tu, San Diego, CA (US)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 0 days.

(21) Appl. No.: 12/247,792

(22) Filed: Oct. 8, 2008

(65) Prior Publication Data

US 2009/0030008 A1    Jan. 29, 2009

Related U.S. Application Data

(62) Division of application No. 10/567,009, filed as application No. PCT/US2004/024658 on Jul. 29, 2004, now Pat. No. 7,456,180.

(60) Provisional application No. 60/491,095, filed on Jul. 30, 2003.

(51) Int. Cl.
    *C07D 239/02*    (2006.01)
(52) U.S. Cl. ........................................ 544/322; 544/359
(58) Field of Classification Search .................. 544/322, 544/359
    See application file for complete search history.

(56) References Cited

U.S. PATENT DOCUMENTS

| 4,423,049 | A | 12/1983 | Temple, Jr. |
| 4,843,078 | A | 6/1989 | Ishizumi et al. |
| 5,444,059 | A | 8/1995 | Frigola-Constansa et al. |
| 5,681,956 | A | 10/1997 | Thurkauf et al. |
| 6,288,230 | B1 | 9/2001 | Chen et al. |
| 7,335,658 | B2 | 2/2008 | Chakka et al. |

FOREIGN PATENT DOCUMENTS

| CA | 983493 A1 | 2/1976 |
| CA | 2476065 A1 | 9/2003 |
| DE | 23 41 925 | 3/1975 |
| EP | 0188094 A2 | 7/1986 |
| EP | 1334972 A1 | 8/2003 |
| EP | 1452525 A1 | 9/2004 |
| JP | 61-043173 A | 3/1986 |
| JP | 61087672 A | 5/1986 |
| WO | 96/16040 A1 | 5/1996 |
| WO | 01/62954 | 8/2001 |
| WO | 01/96327 | 12/2001 |
| WO | 02/10154 | 2/2002 |
| WO | 03/050088 A1 | 6/2003 |
| WO | 03/075929 | 9/2003 |
| WO | 03/076422 A1 | 9/2003 |
| WO | 03/091247 | 11/2003 |
| WO | 03/092686 A1 | 11/2003 |
| WO | 2004/080976 A1 | 9/2004 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Office Action issued Mar. 6, 2009, by the Canadian Intellectual Property Office in related-Canadian Patent Application No. 2,533,901 (7 pages).
Examiner's Report issued Nov. 17, 2009, by the Canadian Intellectual Property Office in related Canadian Patent Application No. 2,533,901 (2 pages) (Note: The references cited in this Examiner's Report have been previously submitted in the IDS filed with the USPTO on Jan. 23, 2009.).
EPO Communication pursuant to Article 94(3) EPC (Office Action) issued Aug. 23, 2010, by the European Patent Office, in related European Patent Application No. EP-04779656.0 (4 pages).
Official Action issued Oct. 26, 2010, by the Japan Patent Office in related Japanese Patent Application No. JP-2006-522096, with English translation (7 pages).
Gotor, V., et al., "Fungal and Bacterial Regioselective Hydroxylation of Pyrimidine Heterocycles"; Tetrahedron, Elsevier Science Publishers, Amsterdam, NL; vol. 53, No. 18 (May 5, 1997); pp. 6421-6432. (Previously submitted in the parent U.S. Appl. No. 10/567,009, filed Jan. 30, 2006, and previously referenced in our IDS filed Jan. 23, 2009.).
Gotor V. et al. "Fungal and Bacterial Regioselective Hydroxylation of Pyrimidine Heterocycles", Tetrahedron, Elsevier Science Publishers, Amsterdam, NL, vol. 53, No. 18, (May 5, 1997), pp. 6421-6432 (previously submitted in U.S. Appl. No. 10/567,009, filed Jan. 30, 2006 (parent application).
International Search Report for PCT/US2004/024658, published Feb. 2, 2005 (4 pages) (previously submitted in U.S. Appl. No. 10/567,009, filed Jan. 30, 2006 (parent application).

(Continued)

Primary Examiner — James O Wilson
Assistant Examiner — Douglas M Willis
(74) Attorney, Agent, or Firm — Seed IP Law Group PLLC

(57) ABSTRACT

Methods of treating an SCD-mediated disease or condition in a mammal, preferably a human, are disclosed, wherein the methods comprise administering to a mammal in need thereof a compound of formula (I):

where G, J, L, M, x, y, W, V, $R^2$, $R^3$, $R^4$, $R^5$, $R^6$, $R^7$, $R^8$, $R^{8a}$, $R^9$, $R^{9a}$, $R^{10}$, $R^{10a}$, $R^{11}$ and $R^{11a}$ are defined herein. Pharmaceutical compositions comprising the compounds of formula (I) are also disclosed.

28 Claims, No Drawings

OTHER PUBLICATIONS

Official Action issued Jul. 14, 2008, by the Canadian Intellectual Property Office in related Canadian Application No. 2,533,901 (3 pages).

Substantive Examination Adverse Report and Search Report dated Dec. 18, 2008, from the Malaysian Patent Office in related-Malaysian Application No. PI-20060382 (3 pages).

Regnier, G. L., et al., "Triphenylpropylpiperazine derivatives as new potent analgetic substances"; Journal of Medicinal Chemistry, Mar. 1972; LNKD-PUBMED: 5059214, vol. 15, No. 3 (Mar. 1972); XP002628470, ISSN: 0022-2623; pp. 295-301.

Awaya, Akira, et al., "Neurotropic Pyrimidine Heterocyclic Compounds. I. The Newly Synthesized Pyrimidine Compounds Promote Neurite Outgrowth of GOTO and Neuro 2a Neuroblastoma Cell Lines, and Potentiate Nerve Growth Factor (NGF)-Induced Neurite Sprouting of PC 12 Cells"; Biological and Pharmaceutical Bulletin, vol. 16, No. 3 (1993); XP002628471, ISSN: 0918-6158; pp. 248-253.

Ishizumi, K., et al., "Synthesis and Anxiolytic Activity of N-Substituted Cyclic Imides (1R*, 2S*, 3R*,4S*)-N-4-4-(2-Pyrimidinyl)-1-piperazinyl]butyl]-2,3-bicyclo[2.2.1]heptanedicarboximide (Tandospirone) and Related Compounds"; Chemical and Pharmaceutical Bulletin (Tokyo), vol. 39, No. 9 (1991); XP002628472, ISSN: 0009-2363; pp. 2288-2300.

Extended European Search Report and Written Opinion dated Mar. 29, 2011, issued by the European Patent Office in related European Patent Application No. 10184745.7 (14 pages).

Official Action issued Jun. 9, 2011, by the State Intellectual Property Office of the People's Republic of China in related Chinese Patent Application No. 200910207686.0, 8 pages.

* cited by examiner

PIPERAZINE DERIVATIVES AS STEAROYL-COA DESATURASE INHIBITORS AND THEIR USE AS THERAPEUTIC AGENTS

CROSS-REFERENCE TO RELATED APPLICATIONS

This application is a Division of application Ser. No. 10/567,009, filed on Jan. 30, 2006 now U.S. Pat. No. 7,456,180, which claims benefit under 35 U.S.C. §120 of PCT/US2004/024658, filed on Jul. 29, 2004, which claims benefits of Provisional (35 U.S.C. §119(e)) application 60/491,095 filed on Jul. 30, 2003. This application claims benefits of all these prior applications and incorporate these prior applications by reference in their entirety.

BACKGROUND OF THE INVENTION

1. Field of the Invention

The present invention relates generally to the field of inhibitors of stearoyl-CoA desaturase, such as piperazine derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

2. Description of Related Art

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the delta-9, delta-6, and delta-5 positions. Stearoyl-CoA desaturases (SCDs) introduce a double bond in the C9-C10 position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (Jeffcoat, R. et al., *Elsevier Science* (1984), Vol. 4, pp. 85-112, de Antueno, R J, *Lipids* (1993), Vol. 28, No. 4, pp. 285-290), it has only recently been directly implicated in human disease processes.

A single SCD gene, SCD1, has been characterized in humans. SCD1 is described in Brownlie et al, PCT published patent application, WO 01/62954, the disclosure of which is hereby incorporated by reference in its entirety. A second human SCD isoform has recently been identified, and because it bears little sequence homology to alternate mouse or rat isoforms it has been named human SCD5 or hSCD5 (PCT published patent application, WO 02/26944, incorporated herein by reference in its entirety).

To date, no small-molecule, drug-like compounds are known that specifically inhibit or modulate SCD activity. Certain long-chain hydrocarbons have been used historically to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA while cis-9, trans-11 conjugated linoleic acid does not. Cyclopropenoid fatty acids, such as those found in stercula and cotton seeds, are also known to inhibit SCD activity. For example, sterculic acid (8-(2-octylcyclopropenyl)octanoic acid) and malvalic acid (7-(2-octylcyclopropenyl)heptanoic acid) are C18 and C16 derivatives of sterculoyl and malvaloyl fatty acids, respectively, having cyclopropene rings at their C9-C10 position. These agents are believed to inhibit SCD enzymatic activity by direct interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety.

These known modulators of delta-9 desaturase activity are not useful for treating the diseases and disorders linked to SCD1 biological activity. None of the known SCD inhibitor compounds are selective for SCD or delta-9 desaturases, as they also inhibit other desaturases and enzymes. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids.

The absence of small molecule inhibitors of SOD enzyme activity is a major scientific and medical disappointment because evidence is now compelling that SCD activity is directly implicated in common human disease processes: See e.g., Attie, A. D. et al, "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al, "Role for stearoyl-CoA desaturase-1 in leptin-mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. USA*. (2002), Vol. 99, No. 7, pp. 11482-6.

The present invention solves this problem by presenting new classes of compounds that are useful in modulating SOD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

Related Literature

PCT Published Patent Applications, WO 03/075929, WO 03/076400 and WO 03/076401, disclose compounds having histone deacetylase inhibiting enzymatic activity.

BRIEF SUMMARY OF THE INVENTION

The present invention provides piperazine derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides methods of inhibiting human stearoyl-CoA desaturase (hSCD) activity comprising contacting a source of hSCD with a compound of formula (I):

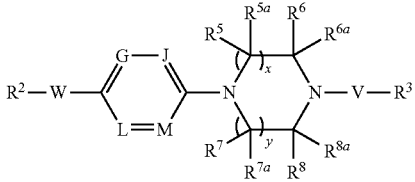

(I)

wherein:

x and y are each independently 1, 2 or 3;

W is —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —N(R$^1$)S(O)$_2$—, —S(O)$_2$N(R$^1$)—, —C(O)—, —OS(O)$_2$N(R$^1$)—, —OC(O)—, —C(O)O— or —N(R$^1$)C(O)O—;

V is —C(O)—, —C(O)O—, —C(S)—, —C(O)N(R$^1$)—, —S(O)$_2$—, —S(O)$_2$N(R$^1$)— or —C(R$^{10}$)H—;

G, J, L and M are each independently selected from —N= or —C(R$^4$)=; provided that at least two of G, J, L and M are —N=, and provided that when G and J are both —C(R$^4$)=, L and M can not both be —N=, and when L and M are both —C(R$^4$)=, G and J can not both be —N=;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

or R$^3$ is a multi-ring structure having 2 to 4 rings wherein the rings are independently selected from the group consisting of cycloalkyl, heterocyclyl, aryl and heteroaryl and where some or all of the rings may be fused to each other;

each R$^4$ is independently selected from hydrogen, fluoro, chloro, methyl, methoxy, trifluoromethyl, cyano, nitro or —N(R$^9$)$_2$;

each R$^5$, R$^{5a}$, R$^6$, R$^{6a}$, R$^7$, R$^{7a}$, R$^8$ and R$^{8a}$ is independently selected from hydrogen or C$_1$-C$_3$alkyl;

or R$^5$ and R$^{5a}$ together, or R$^6$ and R$^{6a}$ together, or R$^7$ and R$^{7a}$ together, or R$^8$ and R$^{8a}$ together are an oxo group, provided that when V is —C(O)—, R$^6$ and R$^{6a}$ together or R$^8$ and R$^{8a}$ together do not form an oxo group, while the remaining R$^5$, R$^{5a}$, R$^6$, R$^{6a}$, R$^7$, R$^{7a}$, R$^8$ and R$^{8a}$ are each independently selected from hydrogen or C$_1$-C$_3$alkyl;

or one of R$^5$, R$^{5a}$, R$^6$, and R$^{6a}$ together with one of R$^7$, R$^{7a}$, R$^8$ and R$^{8a}$ form an alkylene bridge, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl;

R$^{10}$ is hydrogen or C$_1$-C$_3$alkyl; and each R$^9$ is independently selected from hydrogen or C$_1$-C$_6$alkyl;

a stereoisomer, enantiomer or tautomer thereof, a pharmaceutically acceptable salt thereof, a pharmaceutical composition thereof or a prodrug thereof.

In another aspect, the invention provides methods of treating a disease or condition mediated by stearoyl-CoA desaturase (SCD) in a mammal, wherein the method comprises administering to the mammal in need thereof a therapeutically effective amount of a compound of formula (I) as set forth above.

In another aspect, the invention provides compounds of formula (I) having the following formula (II):

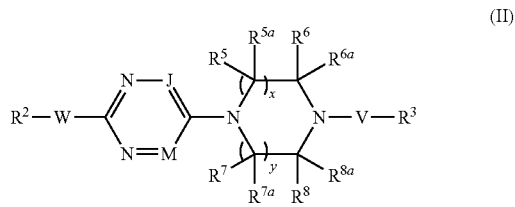

(II)

wherein:

x and y are each independently 1, 2 or 3;

W is —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —N(R$^1$)S(O)$_2$—, —S(O)$_2$N(R$^1$)—, —C(O)—, —OS(O)$_2$N(R$^1$)—, —OC(O)—, —C(O)O— or —N(R$^1$)C(O)O—;

V is —C(O)—, —C(O)O—, —C(S)—, —C(O)N(R$^1$)—, —S(O)$_2$—, —S(O)$_2$N(R$^1$)— or —C(R$^{10}$)H—;

J and M are each independently selected from —N= or —C(R$^4$)=;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

or R$^3$ is a multi-ring structure having 2 to 4 rings wherein the rings are independently selected from the group consisting of cycloalkyl, heterocyclyl, aryl and heteroaryl and where some or all of the rings may be fused to each other;

each R$^4$ is independently selected from hydrogen, fluoro, chloro, methyl, methoxy, trifluoromethyl, cyano, nitro or —N(R$^9$)$_2$;

each R$^5$, R$^{5a}$, R$^6$, R$^{6a}$, R$^7$, R$^{7a}$, R$^8$ and R$^{8a}$ is independently selected from hydrogen or C$_1$-C$_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl; and each $R^9$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (III):

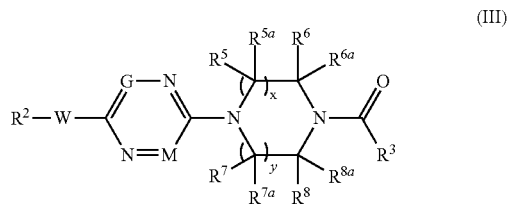

(III)

wherein:

x and y are each independently 1, 2 or 3;

W is —N($R^1$)C(O)—, —C(O)N($R^1$)— or —OC(O)N($R^1$)—;

G and M are each —C($R^4$)=;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$—S(O)$_2$N($R^{12}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen, fluoro, chloro, methyl, methoxy, trifluoromethyl, cyano, nitro or —N($R^9$)$_2$;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together or $R^6$ and $R^{6a}$ together form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

each $R^9$ is independently selected from hydrogen or $C_1$-$C_6$alkyl; and each $R^{12}$ is independently selected from hydrogen, $C_1$-$C_6$alkyl, $C_3$-$C_6$cycloalkyl, aryl or aralkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (IV):

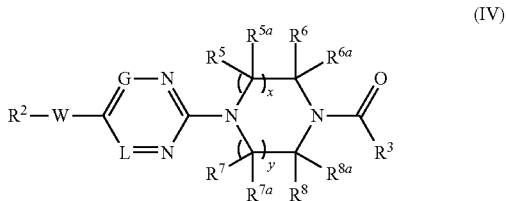

(IV)

wherein:

x and y are each independently 1, 2 or 3;

W is —N($R^1$)C(O)—, —C(O)N($R^1$)— or —OC(O)N($R^1$)—;

G and L are each —C($R^4$)=;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl:

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$-trihaloalkoxy, $C_1$-$C_6$alkylsulfonyl, —N($R^2$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen, fluoro, chloro, methyl, methoxy, trifluoromethyl, cyano, nitro or —N($R^9$)$_2$;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together or $R^7$ and $R^{7a}$ together form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

each $R^9$ is independently selected from hydrogen or $C_1$-$C_6$alkyl; and each $R^{12}$ is independently selected from hydrogen, $C_1$-$C_6$alkyl, $C_3$-$C_6$cycloalkyl, aryl or aralkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (Ia):

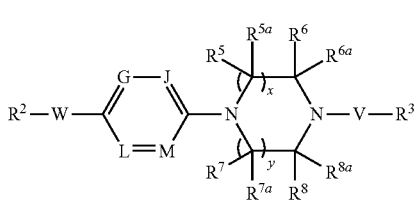

wherein:

x and y are each independently 1, 2 or 3;

W is —N(R$^1$)C(O)N(R$^1$)—, —O—, —N(R$^1$)—, —S(O)$_t$— (where t is 0, 1 or 2), —N(R$^1$)S(O)$_2$—, —S(O)$_2$N(R$^1$)—, —C(O)O— or —N(R$^1$)C(O)O—;

V is —C(O)—, —C(O)O—, —C(S)—, —C(O)N(R$^1$)—, —S(O)$_2$— or —S(O)$_2$N(R$^1$)—;

G, J, L and M are each independently selected from —N= or —C(R$^4$)=; provided that at least two of G O J, L and M are —N=, and provided that when G and J are both —C(R$^4$)=, L and M can not both be —N=, and when L and M are both —C(R$^4$)=, G and J can not both be —N=;

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

or R$^3$ is a multi-ring structure having 2 to 4 rings wherein the rings are independently selected from the group consisting of cycloalkyl, heterocyclyl, aryl and heteroaryl and where some or all of the rings may be fused to each other;

each R$^4$ is independently selected from hydrogen, fluoro, chloro, methyl, methoxy, trifluoromethyl, cyano, nitro or —N(R$^9$)$_2$;

each R$^5$, R$^{5a}$, R$^6$, R$^{6a}$, R$^7$, R$^{7a}$, R$^8$ and R$^{8a}$ is independently selected from hydrogen or C$_1$-C$_3$alkyl;

or R$^5$ and R$^{5a}$ together, or R$^6$ and R$^{6a}$ together, or R$^7$ and R$^{7a}$ together, or R$^8$ and R$^{8a}$ together are an oxo group, provided that when V is —C(O)—, R$^6$ and R$^{6a}$ together or R$^8$ and R$^{8a}$ together do not form an oxo group, while the remaining R$^5$, R$^{5a}$, R$^6$, R$^{6a}$, R$^7$, R$^{7a}$, R$^8$ and R$^{8a}$ are each independently selected from hydrogen or C$_1$-C$_3$alkyl;

or one of R$^5$, R$^{5a}$, R$^6$, and R$^{6a}$ together with one of R$^7$, R$^{7a}$, R$^8$ and R$^{8a}$ form an alkylene bridge, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl; and each R$^9$ is independently selected from hydrogen or C$_1$-C$_6$alkyl;

a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

BRIEF DESCRIPTION OF THE SEVERAL VIEWS OF THE DRAWINGS

Not Applicable

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —$OCH_3$ radical.

"Cyano" refers to the —CN radical.

"Nitro" refers to the —$NO_2$ radical.

"Trifluoromethyl" refers to the —$CF_3$ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocylylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^{14}$—OC(O)—$R^{14}$—$N(R^{14})_2$, —$C(O)R^{14}$—$C(O)OR^{14}$—$CO)N(R^{14})_2$—$N(R^{14})C(O)OR^{16}$, —$N(R^{14})C(O)R^{16}$, —$N(R^{14})(S(O)_tR^{16})$ (where t is 1 to 2), —$S(O)_tOR^{16}$ (where t is 1 to 2), —$S(O)_tR^{16}$ (where t is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to 12 carbon atoms. The $C_3$-$C_{12}$alkenyl radical may be optionally substituted as defined for an alkenyl group.

"$C_2$-$C_{12}$alkenyl" refers to an alkenyl radical as defined above containing two to 12 carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —$OR_a$ where $R_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl part of the $C_3$-$C_{12}$alkoxy radical may be optionally substituted as defined above for an alkyl group.

"Alkoxyalkyl" refers to a radical of the formula —$R_a$—O—$R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —$S(O)_2 R_a$ where $R_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_t R^{16})$ (where t is 1 to 2), —$R^{15}$—$S(O)_t OR^{16}$ (where t is 1 to 2), —$R^{15}$—$S(O)_t R^{16}$ (where t is 0 to 2), and —$R^{15}$—$S(O)_t N(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —$R_a R_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_7$-$C_{19}$aralkyl" refers to an aralkyl group as defined above containing seven to nineteen carbon atoms. The aryl part of the $C_7$-$C_{19}$aralkyl radical may be optionally substituted as described above for an aryl group. The alkyl part of the $C_7$-$C_{19}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —$R_c R_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —$OR_b$ where $R_b$ is an aryl group as defined above. The aryl part of the aryloxy radical may be optionally substituted as defined above.

"Aryl-$C_1$-$C_6$alkyl" refers to a radical of the formula —$R_h$—$R_i$ where $R_h$ is an unbranched alkyl radical having one to six carbons and $R_i$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_t R^{16})$ (where t is 1 to 2), —$R^{15}$—$S(O)_t OR^{16}$ (where t is 1 to 2), —$R^{15}$—$S(O)_t R^{16}$ (where t is 0 to 2), and —$R^{15}$—$S(O)_t N(R^{14})_2$ (where t is 1 to 2) where each $R^{14}$ is independently hydrogen, alkyl haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for an cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^4$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^4$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_aR_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_dR_f$ where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_bR_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to a hydroxyalkyl radical as defined above containing two to twelve carbon atoms. The alkyl part of the $C_2$-$C_{12}$hydroxyalkyl radical may be optionally substituted as defined above for an alkyl group, "$C_3$-$C_{12}$hydroxyalkyl" refers to a hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to a hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula —$R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to a hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to a hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$trihaloalkyl" refers to a trihaloalkyl radical as defined above having one to six carbon atoms. The $C_1$-$C_6$trihaloalkyl may be optionally substituted as defined above for a trihaloalkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"$C_1$-$C_6$trihaloalkoxy" refers to a trihaloalkoxy radical as defined above having one to six carbon atoms. The $C_1$-$C_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure, "Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

Thus, for example, a compound of formula (I), as set forth above in the Summary of the Invention, wherein x and y are each 1; W is —N(R$^1$)C(O)—; V is —C(O)—; J and L are both —N═; G and M are both —C(R$^4$)═; R$^1$, R$^4$, R$^5$, R$^{5a}$, R$^6$, R$^{6a}$, R$^7$, R$^{7a}$, R$^8$ and R$^{8a}$ are each hydrogen; R$^2$ is 2-phenylethyl (phenethyl) and R$^3$ is 2-trifluoromethylphenyl, i.e., a compound of the following formula:

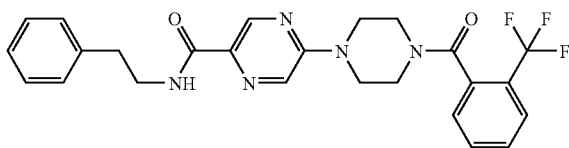

is named herein as 4-(2-Trifluoromethyl-benzoyl)-2,3,5,6-tetrahydro-2H-[1,2']bipyrazinyl-5'-carboxylic acid phenethyl-amide.

Certain radical groups of the compounds of the invention are depicted herein as linkages between two parts of the compounds of the invention. For example, in the following formula (I):

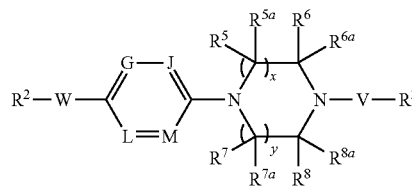

W is described, for example, as being —N(R$^1$)C(O)—, —C(O)N(R$^1$)—, or —N(R$^1$)C(O)N(R$^1$)—; and V is described as —C(O)—, —C(S)— or —C(R$^{10}$)—. This description is meant to describe a W group attached to the R$^2$ group as follows: R$^2$—N(R$^1$)C(O)—, R$^2$—C(O)N(R$^1$)— or R$^2$—N(R$^1$)C(O)N(R$^1$)—; and meant to describe a V group attached to the R$^3$ group as follows: —C(O)—R$^3$, —C(R$^{10}$)—R$^3$, or —C(S)—R$^3$. In other words, the description of the W and V linkage groups are meant to be read from left to right in view of formula (I) as depicted above.

EMBODIMENTS OF THE INVENTION

In one embodiment of the invention, compounds of formula (II), as set forth above in the Summary of the Invention, are directed to compounds wherein x and y are each independently 1, 2 or 3; W is —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —N(R$^1$)S(O)$_2$—, —S(O)$_2$N(R$^1$)—, —C(O)—, —OS(O)$_2$N(R$^1$)—, —OC(O)—, —C(O)O— or —N(R$^1$)C(O)O—; V is —C(O)—, —C(O)O—, —C(S)—, —C(O)N(R$^1$)—, —S(O)$_2$—, —S(O)$_2$N(R$^1$)— or —C(R$^{10}$)H—; J and M are each —C(R$^4$)═; each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl; R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl; R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl; each R$^4$ is independently selected from hydrogen, fluoro, chloro, methyl, methoxy, trifluoromethyl, cyano, nitro or —N(R$^9$)$_2$; each R$^5$, R$^{5a}$, R$^6$, R$^{6a}$, R$^7$, R$^{7a}$, R$^8$ and R$^{8a}$ is independently selected from hydrogen or C$_1$-C$_3$alkyl; or R$^5$ and R$^{5a}$ together, or R$^6$ and R$^{6a}$ together, or R$^7$ and R$^{7a}$ together, or R$^8$ and R$^{8a}$ together are an oxo group, provided that when V is —C(O)—, R$^6$ and R$^{6a}$ together or R$^8$ and R$^{8a}$ together do not form an oxo group, while the remaining R$^5$, R$^{5a}$, R$^6$, R$^{6a}$, R$^7$, R$^{7a}$, R$^8$ and R$^{8a}$ are each independently selected from hydrogen or C$_1$-C$_3$alkyl; or one of R$^5$, R$^{5a}$, R$^6$, and R$^{6a}$ together with one of R$^7$, R$^{7a}$, R$^8$ and R$^{8a}$ form an alkylene bridge, while the remaining R$^5$, R$^{5a}$, R$^6$, R$^{6a}$, R$^7$, R$^{7a}$, R$^8$, and R$^{8a}$ are each independently selected from hydrogen or C$_1$-C$_3$alkyl; and each R$^9$ is independently selected from hydrogen or C$_1$-C$_6$alkyl.

Of this embodiment, one embodiment are compounds wherein x and y are each independently 1, 2 or 3; W is —N(R$^1$)C(O)—; V is —C(O)—; J and M are each —C(R$^4$)═; R$^1$ is selected from the group consisting of hydrogen or C$_1$-C$_{12}$alkyl; each R$^4$ is independently selected from hydrogen, fluoro, chloro, methyl, methoxy, trifluoromethyl, cyano, nitro or —N(R$^9$)$_2$; each R$^5$, R$^{5a}$, R$^6$, R$^{6a}$, R$^7$, R$^{7a}$, R$^8$ and R$^{8a}$ is independently selected from hydrogen or C$_1$-C$_3$alkyl; and each R$^9$ is independently selected from hydrogen or C$_1$-C$_6$alkyl.

Of this embodiment, one embodiment are compounds wherein x and y are each 1; each R$^4$ is hydrogen; and R$^5$, R$^{5a}$, R$^6$, R$^{6a}$, R$^7$, R$^{7a}$, R$^8$ and R$^{8a}$ are each hydrogen.

Of this embodiment, one embodiment are compounds wherein R$^3$ is aryl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$—C(O)O$R^{12}$, —S(O)N($R^{12}$)$_2$, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

Of this embodiment, one embodiment are compounds wherein $R^2$ is $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$cycloalkyl, $C_4$-$C_{12}$cycloalkylalkyl, $C_7$-$C_{19}$aralkyl, $C_3$-$C_{12}$heterocyclylalkyl or $C_3$-$C_{12}$heteroarylalkyl; and $R^3$ is phenyl optionally substituted by one or more substituents selected from halo, $C_1$-$C_6$alkyl, $C_1$-$C_6$trihaloalkyl and $C_1$-$C_6$trihaloalkoxy.

Of this embodiment, one embodiment are compounds wherein $R^2$ is $C_7$-$C_{12}$aralkyl optionally substituted by one or more substituents selected from halo or $C_1$-$C_6$trihaloalkyl.

Of this embodiment, another embodiment are compounds wherein $R^2$ is $C_1$-$C_{12}$alkyl, $C_2$-$C_{12}$alkenyl, $C_2$-$C_{12}$hydroxyalkyl or $C_2$-$C_{12}$hydroxyalkenyl.

Of the main embodiment of compounds of formula (II) as set forth above, another embodiment are compounds wherein x and y are each independently 1, 2 or 3; W is —C(O)N($R^1$)—; V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

Of the main embodiment of compound of formula (II), another embodiment are compounds wherein x and y are each independently 1, 2 or 3; W is —N($R^1$)C(O)N($R^1$)—; V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

Of the main embodiment of compound of formula (II), another embodiment are compounds wherein x and y are each independently 1, 2 or 3; W is —O—, —N($R^1$)— or —S(O)$_t$— (where t is 0, 1 or 2); V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

Of the main embodiment of compound of formula (II), another embodiment are compounds wherein x and y are each independently 1, 2 or 3; W is —N($R^1$)S(O)$_2$— or —S(O)$_2$N($R^1$)—; V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

Of the main embodiment of compound of formula (II), another embodiment are compounds wherein x and y are each independently 1, 2 or 3; W is —C(O)—; V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

Of the main embodiment of compound of formula (II), another embodiment are compounds wherein x and y are each independently 1, 2 or 3; W is —C(O)O— or —N($R^1$)C(O)O—; V is —C(O)—; J and M are each —C($R^4$)=; $R^1$ is selected from the group consisting of hydrogen or $C_1$-$C_{12}$alkyl; each $R^4$ is independently selected from hydrogen, fluoro, chloro, methyl, methoxy, trifluoromethyl, cyano, nitro or —N($R^9$)$_2$; each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^9$ is independently selected from hydrogen or $C_1$-$C_6$alkyl.

One embodiment of the forgoing embodiments are compounds wherein x and y are each 1; each $R^4$ is hydrogen; and $R^5$, $R^{5a}$, $R^6$, $R^{6a}$, $R^7$, $R^{7a}$, $R^8$ and $R^{8a}$ are each hydrogen.

In one embodiment of the invention, compounds of formula (III), as set forth above in the Summary of the Invention, are directed to compounds wherein W is —N($R^1$)C(O)—.

Of this embodiment, one embodiment are compounds wherein x and y are each 1; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^2$)$_2$, —OC(O)$R^2$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl; each $R^4$ is hydrogen; each $R^5$, $R^5$, $R^{5a}$, $R^6$, $R^{6a}$, $R^7$, $R^{7a}$, $R^8$ and $R^{8a}$ is hydrogen; and each $R^{12}$ is independently selected from hydrogen, $C_1$-$C_6$alkyl, $C_3$-$C_6$cycloalkyl, aryl or aralkyl.

Of this embodiment, one embodiment are compounds wherein $R^2$ is independently selected from $C_2$-$C_{12}$alkenyl or $C_1$-$C_{12}$alkyl optionally substituted by —O$R^{12}$; $R^3$ is phenyl optionally substituted by one or more substituents selected from the group consisting of halo $C_1$-$C_6$alkyl, $C_1$-$C_6$trihaloalkyl and $C_1$-$C_6$trihaloalkoxy; and $R^{12}$ is hydrogen, $C_1$-$C_6$alkyl, $C_3$-$C_6$cycloalkyl, aryl or aralkyl.

Of this embodiment, another embodiment are compounds wherein $R^2$ is $C_7$-$C_{12}$aralkyl optionally substituted by one or more substituents selected from the group consisting of halo, $C_1$-$C_6$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

In one embodiment of the invention, compounds of formula (IV), as set forth above in the Summary of the Invention, are directed to compounds wherein W is —N($R^1$)C(O)—.

Of this embodiment, one embodiment are compounds wherein x and y are each 1; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_3$-$C_{12}$heteroaryl and $C_3$-$C_{12}$heteroarylalkyl; $R^3$ is phenyl optionally substituted by one or more substituents selected from the group consisting of halo, cyano, nitro, hydroxy, $C_1$-$C_6$alkyl, $C_1$-$C_6$-trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl; each $R^4$ is hydrogen; each $R^5$, $R^{5a}$, $R^6$, $R^{6a}$, $R^7$, $R^{7a}$, $R^8$ and $R^{8a}$ is hydrogen, and each $R^{12}$ is independently selected from hydrogen, $C_1$-$C_6$alkyl, $C_3$-$C_6$cycloalkyl, aryl or aralkyl.

Of this embodiment, one embodiment are compounds wherein $R^2$ is independently selected from $C_2$-$C_{12}$alkenyl or $C_1$-$C_{12}$alkyl; $R^3$ is phenyl optionally substituted by one or more substituents selected from the group consisting of halo $C_1$-$C_6$alkyl, $C_1$-$C_6$trihaloalkyl and $C_1$-$C_6$trihaloalkoxy; and $R^{12}$ is hydrogen, $C_1$-$C_6$alkyl, $C_3$-$C_6$cycloalkyl, aryl or aralkyl.

Of this embodiment, another embodiment are compounds wherein $R^2$ is $C_7$-$C_{12}$aralkyl optionally substituted by one or more substituents selected from the group consisting of halo, $C_1$-$C_6$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

In one embodiment of the invention, compounds of formula (Ia), as set forth above in the Summary of the Invention, are directed to compounds wherein W is —N($R^1$)C(O)N($R^1$)— and V is —C(O)—.

Of this embodiment, one embodiment are compounds wherein x and y are each 1; each $R^1$ is independently selected from the group consisting of hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; each $R^4$ is hydrogen; and each $R^5$, $R^{5a}$, $R^6$, $R^{6a}$, $R^7$, $R^{7a}$, $R^8$ and $R^{8a}$ is hydrogen.

Of this embodiment, one embodiment are compounds wherein $R^2$ is selected from the group consisting of $C_1$-$C_{12}$alkyl, $C_2$-$C_{12}$alkenyl, $C_4$-$C_{12}$cycloalkylalkyl, $C_7$-$C_{19}$aralkyl, $C_3$-$C_{12}$heterocyclylalkyl and $C_3$-$C_{12}$heteroarylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^2$)$_2$, —OC(O)$R^{12}$, —C(O)O$R^2$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

Specific embodiments of the compounds of the invention are disclosed herein in the following Reaction Schemes and Examples.

In another embodiment, the invention is directed to methods of treating a disease or condition mediated by stearoyl-CoA desaturase (SOD) in a mammal, wherein the method comprises administering to a mammal in need thereof a therapeutically effective amount of a compound of formulae (II), (III), (IV) or (Ia) as set forth above.

In another embodiment, the invention is directed to pharmaceutical compositions comprising a pharmaceutically acceptable excipient and a therapeutically effective amount of a compound of formulae (II), (III), (IV) or (Ia) as set forth above.

In another embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 5. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)).

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids; wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the C9-C10 desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable. ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 µM, preferably below 1 µM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Brownlie et al, supra. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

In general, the compounds of formula (I) of this invention where W is —NHC(O)—, V is —C(O)—, G is —N=, L is —N=, J is —C(R$^4$)= and M is —C(R$^4$)= can be synthesized following the general procedure as described in Reaction Scheme 1.

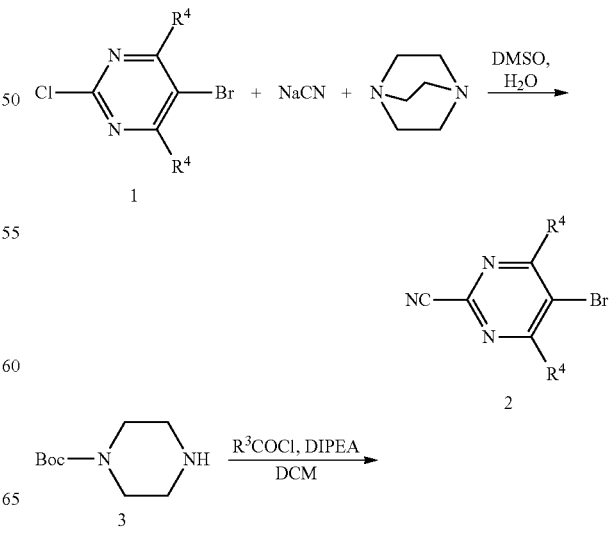

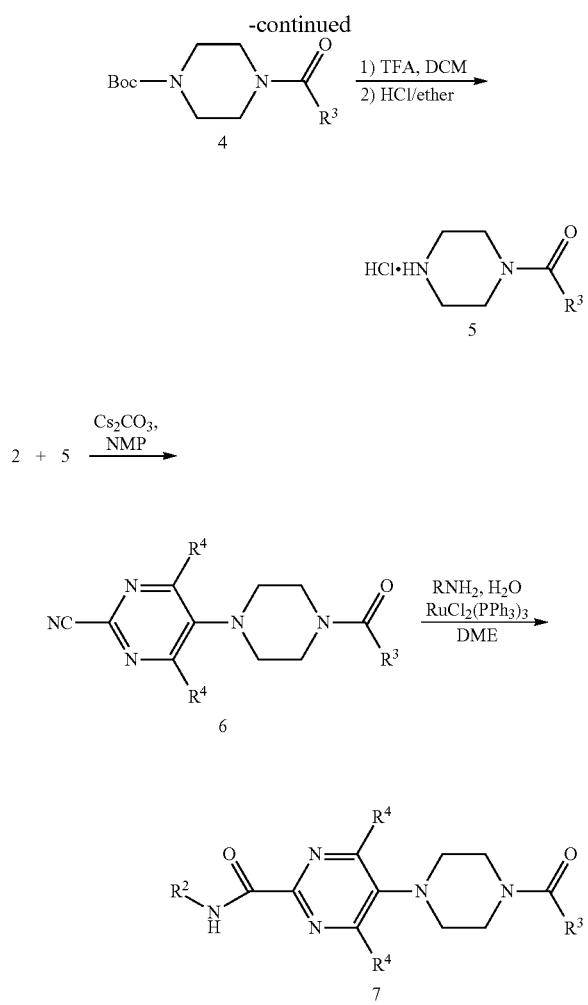

The starting materials for the above reaction scheme are commercially available or can be prepared according to methods known to one skilled in the art or by methods disclosed herein. In general, the compounds of the invention are prepared in the above reaction scheme as follows:

Compound 2. A mixture of 5-bromo-2-chloropyrimidine (1), sodium cyanide, 1,4-diazabicyclo[2,2,2]octane (catalytic amount) in DMSO and water is stirred at room temperature. The reaction is quenched with water and extracted with dichloromethane to yield compound 2.

Compound 5. To a stirred solution of 1-Boc-piperazine (3) in dichloromethane is added appropriate acid chloride as a dichloromethane solution in the presence of N-ethyldiisopropyl amine. The resulting mixture is stirred at RT and then quenched with water. The organic phase is washed with $H_2O$, saturated NaCl, dried over $MgSO_4$ and then concentrated in vacuo to afford product 4. Without further purification, compound 4 is dissolved in excess hydrochloric acid in ether solution, concentrated to yield a colourless solid compound 5.

Compound 6. A mixture of compound 2, 5 and cesium carbonate in NMP is heated. The reaction mixture is cooled to room temperature, concentrated in vacuo, added water, extracted with dichloromethane to yield compound 6.

Compound 7. A mixture of compound 6, appropriate amine and triphenylphosphine rutheniumchloride (catalytic amount) in DME and water is heated. The reaction mixture is cooled to room temperature, solvent is removed in vacuo, added water, extracted with ethyl ether. Organic layer is washed with brine solution, dried over anhydrous sodium sulphate, concentrated to yield compound 7.

Alternatively, compounds of formula (I) of this invention where W is —C(O)NH—, —$SO_2$NH— and —NHC(O)NH—, V is —C(O)—, G is —N═, L is —N═, J is —C($R^4$)═ and M is —C($R^4$)═ can be synthesized following the general procedure as described in Reaction Scheme 2.

REACTION SCHEME 2

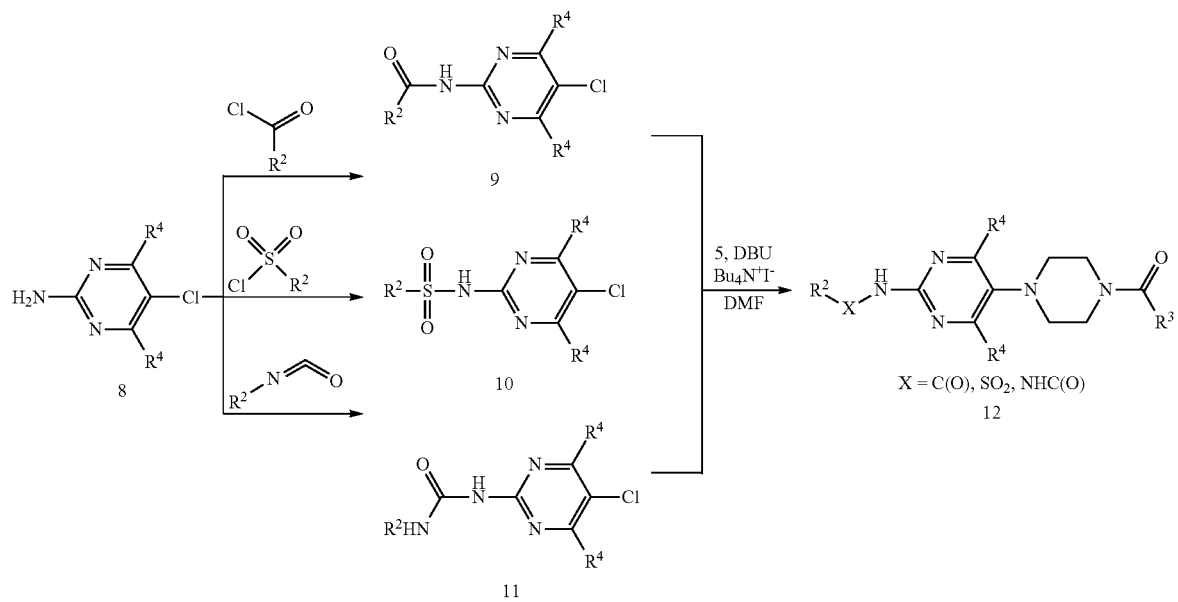

The starting materials for the above reaction scheme are commercially available or can be prepared according to methods known to one skilled in the art or by methods disclosed herein. In general, the compounds of the invention are prepared in the above reaction scheme as follows:

Compounds 9, 10. To a stirred solution of 2-amino-5-chloropyrimidine (8) in dichloromethane is added appropriate acid or sulfonyl chloride as a dichloromethane solution in the presence of triethylamine. The resulting mixture is stirred at RT and then quenched with water. The organic phase is washed with $H_2O$, saturated NaCl, dried over $MgSO_4$ and then concentrated in vacuo to afford product 9 or 10.

Compound 11. To a stirred solution of 2-amino-5-chloropyrimidine (8) in anhydrous ethanol is added appropriate isocyanate in the presence of triethylamine. The resulting mixture is concentrated in vacuo. Crystallization of the residue from ether/hexane afforded product 11.

Compound 12. A solution of compound 9, 10 or 11 in DMF is treated with compound 5. The mixture is diluted with EtOAc. The organic phase is washed with $H_2O$, saturated NaCl, and then dried over $MgSO_4$. The organic phase is concentrated in vacuo to afford product 12.

Alternatively, compounds of formula (I) of this invention W is —C(O)NH—, —$SO_2$NH— and —NHC(O)NH—, V is C(O), G is C($R^4$), L is N, J is N and M is C($R^4$) can be synthesized following the general procedure as described in Reaction Scheme 3.

The starting materials for the above reaction scheme are commercially available or can be prepared according to methods known to one skilled in the art or by methods disclosed herein. In general, the compounds of the invention are prepared in the above reaction scheme as follows:

Compound 14. The mixture of 2-amino-5-chloro-pyrazine (13) and compound 5 is heated. To the reaction mixture, after cooling down to room temperature, is added 1 N NaOH and dichloromethane, and the aqueous layer is extracted with dichloromethane. The combined organic phase is dried over $Na_2SO_4$, evaporated to dryness. The crude compound was purified by flash chromatography to give the desired product 14.

Compound 15. To a stirred solution of compound 14 in anhydrous DMF is added appropriate isocyanate, and the mixture is heated. The mixture is concentrated in vacuo. The crude product is purified by flash chromatography to give the desired product 15.

To a stirred solution of compound 14 in DCM is added appropriate carboxylic chloride, chloroformate or sulfonyl chloride in the presence of triethylamine. The resulting mixture is stirred and then quenched with water. The organic phase is washed with $H_2O$, saturated NaCl, dried over $MgSO_4$ and then concentrated in vacuo to afford the desired product 15.

Alternatively, compounds of formula (I) of this invention W is —NHC(O)—, V is C(O), G is C($R^4$), L is C($R^4$), J is N and M is N can be synthesized following the general procedure as described in Reaction Scheme 4.

REACTION SCHEME 3

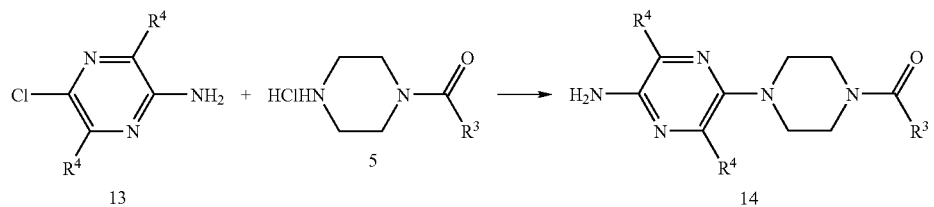

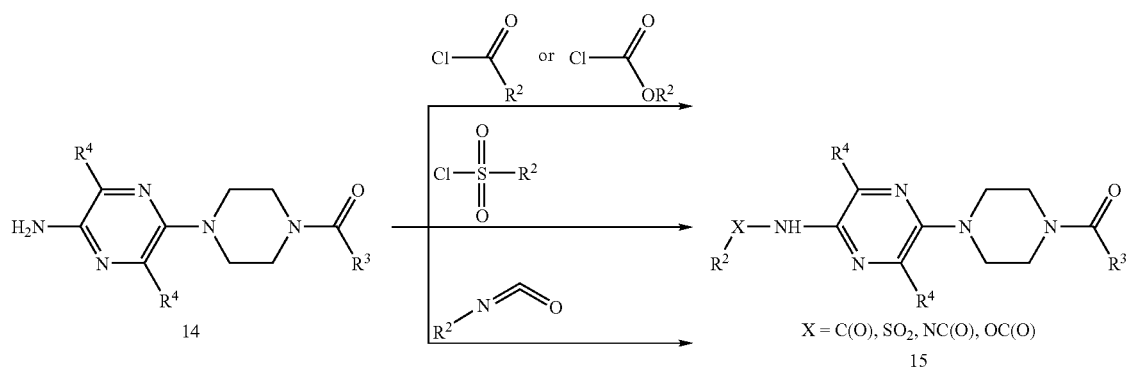

REACTION SCHEME 4

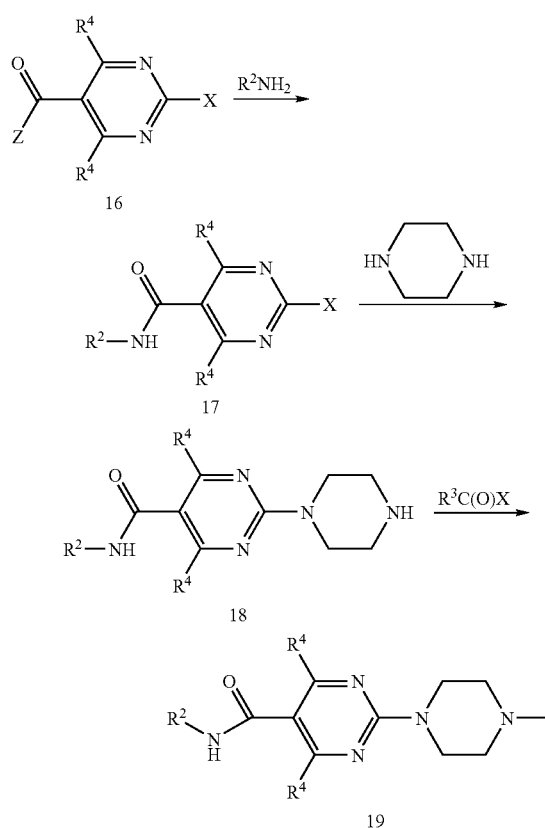

Compound 16 can be used as starting material. In compound 16, X is a leaving group such as chloro or sulfonyl groups. The sulfonyl compound can be prepared starting with X=SMe by oxidation using an oxidant such as, but not limited to, m-chloroperoxybenzoic acid. Z can be hydroxy (acid), alkoxy (ester) or halo (acyl halide). In general, the acid can be obtained by treatment of the corresponding ester by using a base such as, but not limited to lithium hydroxide. The acyl halide such as acyl chloride can be formed by reacting the acid with thionyl chloride. Starting from compound 16, compound 18 can be synthesized either by forming the amide bond first by reacting with an appropriate amine $R^2NH_2$ followed by introduction of the piperazine moiety or vice versa (starting from an ester). Starting from an acid, the coupling conditions such as, but not limited to, hydroxybenzotriazole/1-(3-dimethylaminopropyl)-3-ethylcarbodiimide/diisopropylethylamine/dichloromethane can be used to form the amide by reacting with the amine $R^2NH_2$. Alternatively, starting from an ester, the amide can be produced by mixing the ester with the amine $R^2NH_2$ and heating in microwave, or in the presence of sodium cyanide. Alternatively, starting from an acyl halide such as acyl chloride, the amide can be obtained by reacting with the amine $R^2NH_2$ in the presence of a base such as, but not limited to, triethylamine in a solvent such as, but not limited to, dichloromethane. The piperazine moiety can be introduced by using either piperazine or protected piperazine, for example, tert-butyloxycarbonylpiperazine. If the protected piperazine is used, a deprotection step can be carried out by treatment with an acid such as, but not limited to, trifluoroacetic acid or hydrochloric acid.

Reaction of 18 with an appropriate acyl chloride in the presence of a base such as, but not limited to, diisopropylethylamine in a solvent such as, but not limited to, dichloromethane gives the desired product 19.

Alternatively, compounds of formula (I) of this invention W is —NHC(O)—, V is —C(O)—, G is —N=, L is —C($R^4$)=, J is —C($R^4$)= and M is —N=can be synthesized following the general procedure as described in Reaction Scheme 5.

REACTION SCHEME 5

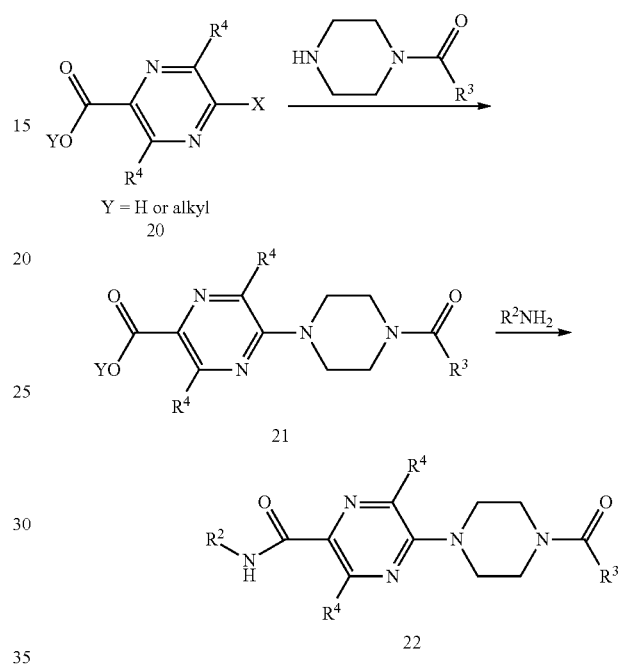

Compound 20 can be used as starting material. In compound 20, X is a leaving group such as chloro group. Reaction of compound 20 with the free base of 5 in the presence of a base such as, but not limited to, potassium carbonate and tetrabutylammonium iodide in a solvent such as, but not limited to, dimethoxyethane affords the formation of compound 21. In compound 21, Y can be hydroxy (acid) or alkoxy (ester). In general, the acid can be obtained by treatment of the corresponding ester by using a base such as, but not limited to lithium hysroxide. Starting from an acid, the coupling conditions such as, but not limited to, hydroxybenzotriazole/1-(3-dimethylaminopropyl)-3-ethylcarbodiimide/diisopropylethylamine/dichloromethane can be used to form the amide 22 by reacting with an appropriate amine $R^2NH_2$. Alternatively, starting from an ester, the amide 22 can be produced by mixing the ester with the amine $R^2NH_2$ and heating in microwave, or in the presence of sodium cyanide.

PREPARATION 1

SYNTHESIS OF PIPERAZIN-1-YL-(2-TRIFLUOROMETHYLPHENYL)METHANONE

A. To a stirred solution of 1-Boc-piperazine (1.96 g, 10.5 mmol) in dichloromethane (50 mL) was added 2-trifluoromethylbenzoyl chloride (2.09 g, 10.0 mmol) as a dichloromethane solution in the presence of triethylamine (3 mL) at 0° C. The resulting mixture was stirred at ambient temperature for 18 hours and then quenched with water (25 mL). The organic phase was washed with water, saturated NaCl, dried over $MgSO_4$ and then concentrated in vacuo to afford the desired product as a pall yellow solid used for next step reaction without further purification.

B. A solution of the compound obtained above (10 mmol) in 50 mL of a 1:4 mixture of trifluoroacetic acid and dichloromethane was stirred at ambient temperature for 5 h. After concentration in vacuo the residue was dissolved in dichloromethane (100 mL) and washed sequentially with 1 N NaOH (10 mL), water, saturated NaCl, and then dried over MgSO4, filtered and concentrated in vacuo to yield piperazin-1-yl-(2-trifluoromethylphenyl)methanone as a light yellow oil. This oil was converted into HCl salt by the addition of 10 mL of 2 N HCl in ether and 100 mL of anhydrous ether to the solution of the compound in 10 mL of dichloromethane. The white solid formed was filtered and dried to yield the HCl salt.

EXAMPLE 1

SYNTHESIS OF 4-TRIFLUOROMETHYL-2-[4-(2-TRIFLUOROMETHYLBENZOYL)PIPERAZIN-1-YL]-PYRIMIDINE-5-CARBOXYLIC ACID (3-METHYLBUTYL)AMIDE

A. To a 20-mL round bottom flask were added Amberlyst A-21 ion-exchange resin (0.836 g, 0.011 mmol), 3-methylbutylamine (0.340 g, 4.0 mmol) and ethyl acetate (42 mL). A solution of 2-chloro-4-trifluoromethyl-pyrimidine-5-carbonyl chloride (1.00 g, 4.0 mmol) in 2.5 mL of ethyl acetate was added. The mixture was stirred for 20 minutes. Water (0.2 mL) was added to the mixture and stirring was continued for another 5 minutes. The solution after filtration was dried over sodium sulfate, concentrated in vacuo. The product obtained was used for next step reaction without further purification (0.846 g, 70% yield).

B. A mixture of 2-chloro-4-trifluoromethylpyrimidine-5-carboxylic acid (3-methylbutyl)amide (0.320 g, 1.10 mmol) obtained above and piperizine (0.280 g, 3.20 mmol) in acetonitrile (25 mL) was heated to reflux for 2 h. The reaction mixture was cooled, washed with water and then concentrated in vacuo. The residue was dissolved in dichloromethane, washed with water, dried over anhydrous MgSO4 and then concentrated in vacuo. The product obtained was used for next step reaction without further purification (0.323 g, yield 86%).

C. To an ice-cold solution of 2-piperazin-1-yl-4-trifluoromethyl-pyrimidine-5-carboxylic acid (3-methylbutyl)amide (0.323 g, 0.935 mmol) in dichloromethane (20 mL) was added diisopropylethylamine (0.242 mL, 1.40 mmol). The mixture was stirred for 10 minutes before 2-trifluoromethylbenzoyl chloride (0.175 g, 0.842 mmol) in 5 mL dichloromethane was added. The stirring was continued for another 15 minutes. The reaction was quenched by the addition of saturated sodium bicarbonate solution, followed by water. The mixture was extracted with dichloromethane, and the organic layer was separated, dried over anhydrous MgSO4 and concentrated in vacuo. The residue was purified by column chromatography to afford the title compound in yield 76% (0.225 g, 0.435 mmol). $^1$H NMR (CDCl$_3$) δ 8.59, 7.73-7.71, 7.64-7.51, 7.35-7.33, 5.76, 4.09-3.74, 3.44-3.37, 3.26-3.22, 1.68-1.59, 1.48-1.41, 0.09. MS (ES+) m/z 518.2 (M+1).

EXAMPLE 1.1

The following compound was synthesized by the synthetic procedure as described in Example 1:

2-[4-(2-Trifluoromethylbenzoyl)piperazin-1-yl]pyrimidine-5-carboxylic acid (3-methylbutyl)amide. MS (ES$^+$) m/z 450 (M+1). $^1$H NMR (300 MHz, CDCl$_3$) δ 8.68, 7.74, 7.71-7.54 (m, 2H), 7.34, 6., 3.97-3.80, 3.46-3.39, 3.25-3.23, 1.65-1.46, 1.45-1.43, 0.93.

EXAMPLE 2

SYNTHESIS OF 4-(2-TRIFLUOROMETHYLBENZOYL)-3,4,5,6-TETRAHYDRO-2H-[1,2']BIPYRAZINYL-5'-CARBOXYLIC ACID PENTYLAMIDE

Potassium tert-butoxide (0.112 g, 1.00 mmol) was added to a premixed mixture of amylamine (2.5 mL) and 4-(2-trifluoromethylbenzoyl)-3,4,5,6-tetrahydro-2H-[1,2']bipyrazinyl-5'-carboxylic acid methyl ester (0.258 g, 0.65 mmol) in a 5 mL reactor for microwave oven. The reaction mixture was irradiated under stirring for 10 minutes at 120° C. On completion of the reaction, the mixture was diluted with water and extracted with dichloromethane. The organic layer was washed sequentially with 10% HCl solution, water and sodium hydroxide solution, then separated and dried with Na$_2$SO$_4$. Removal of the solvent afforded the title compound in 68% yield (0.200 g). $^1$H NMR (300 MHz, CDCl$_3$) δ 8.85, 7.97, 7.74, 7.63, 7.56, 7.49, 7.36, 4.05-4.00, 3.89-3.82, 3.78-3.73, 3.70-3.61, 3.44-3.40, 3.33-3.31, 2.16, 1.63-1.58, 1.37-0.134.

EXAMPLE 2.1

The following compounds were synthesized by the synthetic procedure as described in Example 2.

4-(2-Trifluoromethylbenzoyl)-3,4,5,6-tetrahydro-2H-[1,2']bipyrazinyl-5'-carboxylic acid phenethylamide; $^1$H NMR (300 MHz, CDCl$_3$) δ 8.84, 7.93, 7.67, 7.62-7.53, 7.36-7.21, 4.00, 3.88-3.63, 3.32, 2.92; MS m/z 484.3 (M+1);

4-(2-Trifluoromethylbenzoyl)-3,4,5,6-tetrahydro-2H-[1,2']bipyrazinyl-5'-carboxylic acid (3-phenylpropyl)amide; $^1$H NMR (300 MHz, CD$_3$OD) δ 8.65, 8.21, 3.81, 7.73-7.65, 7.49, 7.25-7.12, 3.90, 3.72, 3.42-3.28, 2.69-2.64, 1.93-1.88; MS m/z 498.4 (M+1);

4-(2-Trifluoromethylbenzoyl)-3,4,5,6-tetrahydro-2H-[1,2']bipyrazinyl-5'-carboxylic acid (3-methylbutyl)amide; $^1$H NMR (300 MHz, CDCl$_3$) δ 8.84, 7.95, 7.73, 7.62-7.55, 7.44, 7.35, 4.02-3.99, 3.90-3.63, 3.49-3.42, 3.34-3.30, 1.71-1.47, 0.95; MS m/z 450.1 (M+1);

4-(2-Trifluoromethylbenzoyl)-3,4,5,6-tetrahydro-2H-[1,2']bipyrazinyl-5'-carboxylic acid [2-(4-fluorophenyl)ethyl]amide; $^1$H NMR (300 MHz, CDCl$_3$) δ 8.83, 7.93, 7.73, 7.62-7.52, 7.35, 7.24-7.15, 6.97-6.94, 4.01-3.99, 3.89-3.63, 3.32, 2.89; MS m/z 502.3 (M+1).

EXAMPLE 3

SYNTHESIS OF 5-[4-(2-TRIFLUOROMETHYLBENZOYL)PIPERAZIN-1-YL]-PYRIMIDINE-2-CARBOXYLIC ACID (3-PHENYLPROPYL) AMIDE

A. To a vial containing sodium cyanide (0.27 g, 5.43 mmol) and DABCO (0.087 g, 0.80 mmol) in 3 mL of water was added DMSO (3 mL) under nitrogen atmosphere, followed by the addition of 5-bromo-2-chloropyrimidine (1.00 g, 5.17 mmol) in DMSO (3 mL). The reaction mixture gradually turned to brown over 2 h. It was diluted with ethyl acetate (75 mL), washed sequentially with water, 1 N HCl, saturated NaHCO$_3$ solution and brine, dried over MgSO$_4$, filtered and concentrated in vacuo to yield the product as a yellow solid (0.843 g, 89% yield). MS m/z 183.9 (M+1).

B. A mixture of 5-bromopyrimidine-2-carbonitrile (0.86 g, 4.6 mmol) obtained above, $CsCO_3$ (6.0 g, 18 mmol) and piperazin-1-yl-(2-trifluoromethylphenyl)-methanone (1.35 g, 4.6 mmol) in 20 mL of anhydrous NMP was heated to 80° C. overnight. After removal of the solvent, the residue was dissolved in ethyl acetate (150 mL), which was washed with 1 N HCl, saturated $NaHCO_3$ solution, brine, and then dried over anhydrous $MgSO_4$. The residue obtained after removal of the solvent was purified by column chromatography. The product, 5-[4-(2-trifluoromethylbenzoyl)piperazin-1-yl]-pyrimidine-2-carbonitrile, was obtained in 38% yield (0.63 g). MS m/z 362.2 (M+1).

C. A mixture of 5-[4-(2-trifluoromethylbenzoyl)piperazin-1-yl]-pyrimidine-2-carbonitrile (0.050 g, 0.14 mmol) obtained above, 3-phenylpropylamine (0.040 mg, 0.28 mmol), water (5 μL, 0.28 mmol), and dichlorotris(triphenylphosphine)ruthenium(II) (4 mg, 0.004 mmol) in 1,2-dimethoxyethane (0.2 mL) was heated to 160° C. for three days. The reaction mixture was diluted with dichloromethane and then loaded onto a preparative thin layer chromatography plate which was developed using ethyl acetate:hexanes=4:1 to afford crude compound. The pure compound was obtained after recrystallization from isopropyl alcohol in 5% yield (3.2 mg). $^1$H NMR (300 MHz, $CDCl_3$) δ 8.39, 7.80, 7.75, 7.68-7.53, 7.38-7.15, 4.15-3.90, 3.59-3.38, 3.25, 2.70, 1.99. MS m/z 497.6 (M).

EXAMPLE 3.1

The following compounds were synthesized by the synthetic processes as described in Example 3:

5-[4-(2-Trifluoromethylbenzoyl)piperazin-1-yl]pyrimidine-2-carboxylic acid phenethylamide. $^1$H NMR (300 MHz, $CDCl_3$) δ 8.35 (s, 1H), 7.83-7.31 (m, 4H), 7.29-7.21 (m, 7H), 4.06-3.93 (m, 2H), 3.79-3.72 (m, 2H), 3.48-3.25 (m, 6H), 2.96-2.91 (m, 2H). MS (ES+) m/z 484 (M+1).

5-[4-(2-Trifluoromethylbenzoyl)piperazin-1-yl]pyrimidine-2-carboxylic acid hexylamide. $^1$H NMR (300 MHz, $CDCl_3$) δ 8.39, 7.81-7.72, 7.69-7.52, 7.39-7.36, 4.16-3.88, 3.71-3.21, 1.65-1.58, 1.42-1.22, 0.95-0.91. MS (ES+) m/z 464 (M+1).

5-[4-(2-Trifluoromethylbenzoyl)piperazin-1-yl]pyrimidine-2-carboxylic acid benzylamide. $^1$H NMR (300 MHz, $CDCl_3$) δ 8.39, 8.15, 7.68, 7.45-7.62, 7.29-7.21, 4.65-4.62, 4.18-3.95, 3.46-3.21 MS (ES+) m/z 470 (M+1).

EXAMPLE 4

The following compounds are synthesized by the synthetic processes as described above;
4-(2-Trifluoromethyl-benzoyl)-3,4,5,6-tetrahydro-2H-[1,2'] bipyrazinyl-5'-carboxylic acid (2-phenoxy-ethyl)-amide;
4-(2-Trifluoromethyl-benzoyl)-3,4,5,6-tetrahydro-2H-[1,2'] bipyrazinyl-5'-carboxylic acid [3-(4-fluoro-phenyl)-propyl]-amide; and
4-(2-Trifluoromethyl-benzoyl)-3,4,5,6-tetrahydro-2H-[1,2'] bipyrazinyl-5'-carboxylic acid [3-(4-fluoro-phenyl)-propyl]-amide.

EXAMPLE 5

Measuring Stearoyl-CoA Desaturase Inhibition Activity of a Test Compound Using Mouse Liver Microsomes The identification of compounds of the invention as SCD inhibitors was readily accomplished using the SCD enzymes and microsomal assay procedure described in Brownlie et al, PCT published patent application, WO 01/62954.

Preparation of Mouse Liver Microsomes:

Male ICR mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 1.5 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Reactions are started by adding 2 mg of microsomal protein to pre-incubated tubes containing 0.20 μCi of the substrate fatty acid (1-$^{14}$C palmitic acid) at a final concentration of 33.3 μM in 1.5 ml of homogenization solution, containing 42 mM NaF, 0.33 mM niacinamide, 1.6 mM ATP, 1.0 mM NADH, 0.1 mM coenzyme A and a 10 μM concentration of test compound. The tubes are vortexed vigorously and after 15 min incubation in a shaking water bath (37° C.), the reactions are stopped and fatty acids are analyzed.

Fatty acids are analyzed as follows: The reaction mixture is saponified with 10% KOH to obtain free fatty acids which are further methylated using $BF_3$ in methanol. The fatty acid methyl esters are analyzed by high performance liquid chromatography (HPLC) using a Hewlett Packard 1090, Series II chromatograph equipped with a diode array detector set at 205 nm, a radioisotope detector (Model 171, Beckman, Calif.) with a solid scintillation cartridge (97% efficiency for $^{14}$C-detection) and a reverse-phase ODS (C-18) Beckman column (250 mm×4.6 mm i.d.; 5 μm particle size) attached to a pre-column with a μBondapak C-18 (Beckman) insert. Fatty acid methyl esters are separated isocratically with acetonitrile/water (95:5 v:v) at a flow rate of 1 mL/min and are identified by comparison with authentic standards. Alternatively, fatty acid methyl esters may be analyzed by capillary column gas-chromatography (GC) or Thin Layer Chromatography (TLC).

Those skilled in the art are aware of a variety of modifications to this assay that can be useful for measuring inhibition of stearoyl-CoA desaturase activity in microsomes by test compounds.

Representative compounds of the invention showed activity as inhibitors of SCD when tested in this assay. The activity was defined in terms of % SCD enzyme activity remaining at the desired concentration of the test compound.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound of formula (II):

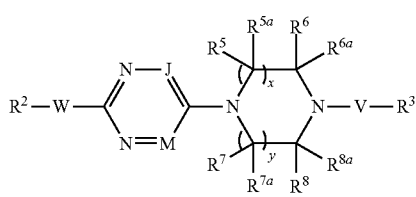

wherein:
x and y are each independently 1;
W is —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_2$—, —S(O)$_2$N($R^1$)—, —C(O)—, —OS(O)$_2$N($R^1$)—, —OC(O)—, —C(O)O— or —N($R^1$)C(O)O—;
V is —C(O)—, —C(O)O—, —C(S)—, —C(O)N($R^1$)—, or —C($R^{10}$)H—;
J and M are each —C($R^4$)═;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
or $R^2$ is a multi-ring structure having 2 to 4 rings wherein the rings are independently selected from the group consisting of cycloalkyl, heterocyclyl, aryl and heteroaryl and where some or all of the rings may be fused to each other;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
or $R^3$ is a multi-ring structure having 2 to 4 rings wherein the rings are independently selected from the group consisting of cycloalkyl, heterocyclyl, aryl and heteroaryl and where some or all of the rings may be fused to each other;
each $R^4$ is hydrogen;
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and
$R^{10}$ is hydrogen or $C_1$-$C_3$alkyl;
wherein each of $C_1$-$C_3$alkyl, $C_1$-$C_{12}$alkyl, $C_2$-$C_{12}$hydroxyalkyl, and $C_2$-$C_{12}$alkoxyalkyl is optionally substituted by one of the following groups: $C_1$-$C_{12}$alkyl, $C_2$-$C_{12}$alkenyl, halo, $C_2$-$C_{12}$haloalkenyl, cyano, nitro, $C_6$-$C_{19}$aryl, $C_3$-$C_{12}$cycloalkyl, $C_3$-$C_{12}$heterocyclyl, $C_1$-$C_{12}$heteroaryl, —O$R^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)S(O)$_t$$R^{16}$) (where t is 1 to 2), —S(O)$_t$OR$^{16}$ (where t is 1 to 2), —S(O)$_t$$R^{16}$ (where t is 0 to 2), and —S(O)$_t$N($R^{14}$)$_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl (optionally substituted with one or more halo groups), $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;
wherein $C_2$-$C_{12}$alkenyl or $C_2$-$C_{12}$hydroxyalkenyl is optionally substituted by one of the following groups: $C_1$-$C_{12}$alkyl, $C_2$-$C_{12}$alkenyl, halo, halo$C_1$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —O$R^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$) (where t is 1 to 2), —S(O)$_t$OR$^{16}$ (where t is 1 to 2), —S(O)$_t$$R^{16}$ (where t is 0 to 2), and —S(O)$_t$N($R^{14}$)$_2$ (where t is 1 to 2 where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heteroarylalkyl, $C_1$-$C_{12}$heteroaryl or $C_3$-$C_{12}$heteroarylalkyl; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;
wherein each of $C_3$-$C_{12}$cycloalkyl and the cycloalkyl part of $C_4$-$C_{12}$cycloalkylalkyl is optionally substituted b one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$OR$^{19}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;
wherein each of $C_6$-$C_{19}$aryl or the aryl part of $C_7$-$C_{19}$aralkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—$OR^{14}$, —$R^{15}OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2) —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein each of $C_3$-$C_{12}$heterocyclyl or the heterocyclyl part of $C_3$-$C_{12}$heterocyclylalkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, oxo, thioxo, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, $C_1$-$C_{12}$alkyl, $C_2$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein each of $C_1$-$C_{12}$heteroaryl or the heteroaryl part of $C_3$-$C_{12}$heteroarylalkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, oxo, thioxo, nitro, $C_6$-$C_{19}$aryl, $C_7$-$C_{19}$aralkyl, $C_3$-$C_{12}$cycloalkyl, $C_4$-$C_{12}$heteroalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, $R^{15}$—$N(R^{14})S(O)_tR^{16}$) (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, $C_1$-$C_{12}$alkyl, $C_2$-$C_{12}$alkenyl, halo$C_1$-$C_{12}$alkyl, —$C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted; and a stereoisomer, or tautomer thereof, or a pharmaceutically acceptable salt thereof.

2. The compound of claim 1 wherein:

x and y are each independently 1;

W is —$N(R^1)C(O)$—, —$C(O)N(R^1)$—, —$OC(O)N(R^1)$—, —$N(R^1)C(O)N(R^1)$—, —O—, —$N(R^1)$—, —$S(O)_t$— (where t is 0, 1 or 2), —$N(R^1)S(O)_2$—, —$S(O)_2N(R^1)$—, —$C(O)$—, —$OS(O)_2N(R^1)$—, —$OC(O)$—, —$C(O)O$— or —$N(R^1)C(O)O$—;

V is —$C(O)$—, —$C(O)O$—, —$C(S)$—, —$C(O)N(R^1)$—, or —$C(R^{10})H$—;

J and M are each —$C(R^4)$=;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; and each $R^4$ is hydrogen;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

3. The compound of claim 2 wherein:

x and y are each independently 1;

W is —$N(R^1)C(O)$—;

V is —$C(O)$—;

J and M are each —$C(R^4)$=;

$R^1$ is selected from the group consisting of hydrogen and $C_1$-$C_{12}$alkyl;

each $R^4$ is; and each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

4. The compound of claim 3 wherein:

x and y are each 1;

each $R^4$ is hydrogen; and $R^5$, $R^{5a}$, $R^6$, $R^{6a}$, $R^7$, $R^{7a}$, $R^8$ and $R^{8a}$ are each hydrogen.

5. The compound of claim 4 wherein:

$R^3$ is aryl optionally substituted by one or more substituents selected from the group consisting of halo, cyano, nitro, $C_1$-$C_6$alkyl, $C_1$-$C_6$trihaloalkyl, $C_1$-$C_6$alkylsulfonyl, —$N(R^{12})_2$, —$OC(O)R^{12}$, —$C(O)OR^{12}$, —$S(O)_2N(R^{14})_2$, $C_3$-$C_{12}$cycloalkyl, $C_3$-$C_{12}$heterocyclyl and $C_1$-$C_{12}$heteroaryl; and each $R^{12}$ is independently selected from hydrogen, $C_1$-$C_6$alkyl, $C_3$-$C_6$cycloalkyl, aryl or aralkyl.

6. The compound of claim 5 wherein:
$R^2$ is $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$cycloalkyl, $C_4$-$C_{12}$cycloalkylalkyl, $C_7$-$C_{19}$aralkyl, $C_3$-$C_{12}$heterocyclylalkyl or $C_3$-$C_{12}$heteroarylalkyl; and
$R^3$ is phenyl optionally substituted by one or more substituents selected from halo, $C_1$-$C_6$alkyl, $C_1$-$C_6$trihaloalkyl and $C_1$-$C_6$trihaloalkoxy.

7. The compound of claim 6 wherein $R^2$ is $C_7$-$C_{12}$aralkyl optionally substituted by one or more substituents selected from halo or $C_1$-$C_6$-trihaloalkyl.

8. The compound of claim 7 selected from the group consisting of the following:
5-[4-(2-Trifluoromethyl-benzoyl)-piperazin-1-yl]-pyrimidine-2-carboxylic acid phenethyl-amide;
5-[4-(2-Trifluoromethyl-benzoyl)-piperazin-1-yl]-pyrimidine-2-carboxylic acid (3-phenyl-propyl)-amide; and
5-[4-(2-Trifluoromethyl-benzoyl)-piperazin-1-yl]-pyrimidine-2-carboxylic acid benzylamide.

9. The compound of claim 6 wherein $R^2$ is $C_1$-$C_{12}$alkyl, $C_2$-$C_{12}$alkenyl, $C_2$-$C_{12}$hydroxyalkyl or $C_2$-$C_{12}$hydroxyalkenyl.

10. The compound of claim 9, wherein the compound is 5-[4-(2-Trifluoromethyl-benzoyl)-piperazin-1-yl]-pyrimidine-2-carboxylic acid hexylamide.

11. The compound of claim 2 wherein:
x and y are each independently 1;
W is —C(O)N($R^1$)—;
V is —C(O)—;
J and M are each —C($R^4$)=;
$R^1$ is selected from the group consisting of hydrogen or $C_1$-$C_1C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

12. The compound of claim 11, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

13. The compound of claim 2 wherein:
x and y are each independently 1;
W is —N($R^1$)C(O)N($R^1$)—;
V is —C(O)—;
J and M are each —C($R^4$)=;
$R^1$ is selected from the group consisting of hydrogen or $C_1$-$C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

14. The compound of claim 13, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

15. The compound of claim 2 wherein:
x and y are each independently 1;
W is —O—, —N($R^1$)— or —S(O)$_t$— (where t is 0, 1 or 2);
V is —C(O)—;
J and M are each —C($R^4$)=;
$R^1$ is selected from the group consisting of hydrogen or $C_1$-$C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

16. The compound of claim 15, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

17. The compound of claim 2 wherein:
x and y are each independently 1;
W is —N($R^1$)S(O)$_2$— or —S(O)$_2$N($R^1$)—;
V is —C(O)—;
J and M are each —C($R^4$)=;
$R^1$ is selected from the group consisting of hydrogen or $C_1$-$C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

18. The compound of claim 17, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

19. The compound of claim 2 wherein:
x and y are each independently 1;
W is —C(O)—;
V is —C(O)—;
J and M are each —C($R^4$)=;
$R^1$ is selected from the group consisting of hydrogen or $C_1$-$C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alky.

20. The compound of claim 19, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

21. The compound of claim 2 wherein:
x and y are each independently 1;
W is —C(O)O— or —N($R^1$)C(O)O—;
V is —C(O)—;
J and M are each —C($R^4$)=;
$R^1$ is selected from the group consisting of hydrogen or $C_1$-$C_{12}$alkyl;
each $R^4$ is hydrogen; and
each $R^5$, $R^{5a}$, $R^6$, $R^{6a}$, $R^7$, $R^{7a}$, $R^8$ and $R^{8a}$ is independently selected from hydrogen or $C_1$-$C_3$alkyl.

22. The compound of claim 21, wherein:
x and y are each 1;
each $R^4$ is hydrogen; and
$R^5$, $R^{5a}$, $R^6$, $R^{6a}$, $R^7$, $R^{7a}$, $R^8$ and $R^{8a}$ are each hydrogen.

23. A compound of formula (IV):

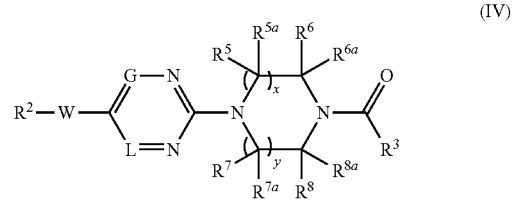

wherein:
x and y are each independently 1;
W is —N($R^1$)C(O)—, —C(O)N($R^1$)— or —OC(O)N($R^1$)—;
G and L are each —C($R^4$)=;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen, or trifluoromethyl;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl; and each $R^{12}$ is independently selected from hydrogen, $C_1$-$C_6$alkyl, $C_3$-$C_6$cycloalkyl, aryl or aralkyl;

wherein each of $C_1$-$C_3$alkyl, $C_1$-$C_{12}$alkyl, $C_2$-$C_{12}$hydroxyalkyl, and $C_2$-$C_{12}$alkoxyalkyl is optionally substituted by one of the following groups: $C_1$-$C_{12}$alkyl, $C_2$-$C_{12}$alkenyl, halo, $C_2$-$C_{12}$haloalkenyl, cyano, nitro, $C_6$-$C_{19}$aryl, $C_3$-$C_{12}$cycloalkyl, $C_3$-$C_{12}$heterocyclyl, $C_1$-$C_{12}$heteroaryl, —O$R^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$) (where t is 1 to 2), —S(O)$_t$O$R^{16}$ (where t is 1 to 2), —S(O)$_t$$R^{16}$ (where t is 0 to 2), and —S(O)$_t$N($R^{14}$)$_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl (optionally substituted with one or more halo groups), $C_7$-$C_{19}$aralkyl, $C_3$-$C_{12}$heterocycyl, $C_3$-$C_{12}$heterocyclylalkyl, $C_1$-$C_{12}$heteroaryl or $C_3$-$C_{12}$heteroarylalkyl; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein $C_2$-$C_{12}$alkenyl or $C_2$-$C_{12}$hydroxyalkenyl is optionally substituted by one of the following groups: $C_1$-$C_{12}$alkyl, $C_2$-$C_{12}$alkenyl, halo, halo$C_1$-$C_{12}$alkyl, halo$C_2$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —O$R^{14}$, —OC(O)—$R^{14}$, —N$R^{14}$$_2$, —C(O)$R^{14}$, —C(O)O$R^{14}$, —C(O)N($R^{14}$)$_2$, —N$R^{14}$C(O)O$R^{16}$, —N($R^{14}$)C(O)$R^{16}$, N($R^{14}$)(S(O)$_t$$R^{16}$) (where t is 1 to 2), —S(O)$_t$O$R^{16}$ (where t is 1 to 2), —S(O)$_t$$R^{16}$ (where t is 0 to 2), and —S(O)$_t$N($R^{14}$)$_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, halo$C_1$-$C_{12}$alkyl, $C_3$-$C_{12}$heterocyclylalkyl, $C_1$-$C_{12}$heteroaryl or $C_3$-$C_{12}$heteroarylalkyl; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein each of $C_3$-$C_{12}$cycloalkyl and the cycloalkyl part of $C_4$-$C_{12}$cycloalkylalkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$), (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted wherein each of $C_6$-$C_{19}$aryl or the aryl part of $C_7$-$C_{19}$aralkyl is optionally substituted by one or more substituents selected from the group consisting of $C_1$-$C_2$alkyl, $C_2$-$C_{12}$alkenyl, halo, halo$C_1$-$C_{12}$alkyl, halo$C_2$-$C_{12}$alkenyl, cyano, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein each of $C_3$-$C_{12}$heterocyclyl or the heterocyclyl part of $C_3$-$C_{12}$heterocyclylalkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, oxo, thioxo, nitro $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{16}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$OR$^{16}$ (where t is 1 to 2), —$R^{15}$—S(O)$_t$R$^{16}$ (where t is 0 to 2), and —$R^{15}$—S(O)$_t$N(R$^{14}$)$_2$ (where t is 1 to 2) where each $R^{14}$ is independently hydrogen, $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted;

wherein each of $C_1$-$C_{12}$heteroaryl or the heteroaryl art of $C_3$-$C_{12}$heteroarylalkyl is optionally substituted by one or more substituents selected from the group consisting of $C_1$-$C_{12}$alkyl, $C_2$-$C_{12}$alkenyl, halo, halo$C_1$-$C_{12}$alkyl, halo$C_2$-$C_{12}$alkenyl, cyano, oxo, thioxo, nitro, $C_6$-$C_{19}$aryl, $C_7$-$C_{19}$aralkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, $C_1$-$C_{12}$heteroaryl, $C_3$-$C_{12}$heteroarylalkyl, —$R^{15}$—OR$^{14}$, —$R^{15}$—OC(O)—R$^{14}$, —$R^{15}$—N(R$^{14}$)$_2$, —$R^{15}$—C(O)R$^{14}$, —$R^{15}$—C(O)OR$^{14}$, —$R^{15}$—C(O)N(R$^{14}$)$_2$, —$R^{15}$—N(R$^{14}$)C(O)OR$^{16}$, —$R^{15}$—N(R$^{14}$)C(O)R$^{16}$, —$R^{15}$—N(R$^{14}$)(S(O)$_t$R$^{16}$) (where t is 1 to 2), —$R^{15}$—S(O)$_t$OR$^{16}$ (where t is 1 to 2), —$R^{15}$—S(O)$_t$R$^{16}$ (where t is 0 to 2), and —$R^{15}$—S(O)$_t$N(R$^{14}$)$_2$ (where t is 1 to 2 where each $R^{14}$ is independently hydrogen, $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl; each $R^{15}$ is independently a direct bond or a straight or branched $C_1$-$C_{12}$alkylene or $C_2$-$C_{12}$alkenylene chain; and each $R^{16}$ is $C_1$-$C_{12}$alkyl, $C_2$-$C_{12}$alkenyl, halo$C_1$-$C_{12}$alkyl, $C_3$-$C_{12}$cycloalkyl, $C_4$-$C_{12}$cycloalkylalkyl, $C_6$-$C_{19}$aryl, $C_7$-$C_{19}$aralkyl, $C_3$-$C_{12}$heterocyclyl, $C_3$-$C_{12}$heterocyclylalkyl, $C_1$-$C_{12}$heteroaryl or $C_3$-$C_{12}$heteroarylalkyl, and where each of the above substituents is unsubstituted; and a stereoisomer, or tautomer thereof, or a pharmaceutically acceptable salt thereof.

24. The compound of claim 23 wherein W is —N(R$^1$)C(O)—.

25. The compound of claim 24 wherein:

x and y are each 1;

$R^1$ is hydrogen or $C_1$-$C_6$alkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^3$ is phenyl optionally substituted by one or more substituents selected from the group consisting of halo, cyano, nitro, hydroxy, $C_1$-$C_6$alkyl, $C_1$-$C_6$-trihaloalkyl, $C_1$-$C_6$-trihaloalkoxy, $C_1$-$C_6$alkylsulfonyl, —N(R$^{12}$)$_2$, —OC(O)R$^{12}$, —C(O)OR$^{12}$, —S(O)$_2$N(R$^{12}$)$_2$, cycloalkyl, heterocyclyl, heteroaryl and heteroarylcycloalkyl, provided that $R^3$ is not phenyl substituted with optionally substituted thienyl;

each $R^4$ is independently selected from hydrogen or trifluoromethyl;

each $R^5$, $R^{5a}$, $R^6$, $R^{6a}$, $R^7$, $R^{7a}$, $R^8$ and $R^{8a}$ is hydrogen; and each $R^{12}$ is independently selected from hydrogen, $C_1$-$C_6$alkyl, $C_3$-$C_6$cycloalkyl, aryl or aralkyl.

26. The compound of claim 25 wherein:

$R^2$ is $C_7$-$C_{12}$aralkyl optionally substituted by one or more substituents selected from the group consisting of halo, $C_1$-$C_6$alkyl and $C_1$-$C_6$-trihaloalkyl; and $R^3$ is phenyl optionally substituted by one or more substituents selected from the group consisting of halo, $C_1$-$C_6$alkyl, $C_1$-$C_6$-trihaloalkyl and $C_1$-$C_6$-trihaloalkoxy.

27. The compound of claim 25 wherein:

$R^2$ is independently selected from $C_2$-$C_{12}$alkenyl or $C_1$-$C_{12}$alkyl;

$R^3$ is phenyl optionally substituted by one or more substituents selected from the group consisting of halo $C_1$-$C_6$alkyl, $C_1$-$C_6$-trihaloalkyl and $C_1$-$C_6$-trihaloalkoxy; and $R^{12}$ is hydrogen, $C_1$-$C_6$alkyl, $C_3$-$C_6$cycloalkyl, aryl or aralkyl.

28. The compound of claim 27 selected from the group consisting of the following:

4-trifluoromethyl-2-[4-(2-trifluoromethylbenzoyl)piperazin-1-yl]-pyrimidine-5-carboxylic acid (3-methylbutyl)amide; and 2-[4-(2-Trifluoromethylbenzoyl)piperazin-1-yl]pyrimidine-5-carboxylic acid (3-methylbutyl)amide.

* * * * *

UNITED STATES PATENT AND TRADEMARK OFFICE
CERTIFICATE OF CORRECTION

PATENT NO.           : 8,030,488 B2
APPLICATION NO.  : 12/247792
DATED                    : October 4, 2011
INVENTOR(S)         : Serguei Sviridov et al.

It is certified that error appears in the above-identified patent and that said Letters Patent is hereby corrected as shown below:

Column 41, Line 35:
"$C_r$-$C_{19}$aralkyl" should read, --$C_7$-$C_{19}$aralkyl--.

Column 41, Line 67:
"-$N(R^{14})S(O)_tR^{16}$)" should read, -- -$N(R^{14})(S(O)_tR^{16}$--.

Column 42, Line 25:
"and $-S(O)_tN(R^{14})_2$ (where t is 1 to 2 where each $R^{14}$ is" should read, --and $-S(O)_tN(R^{14})_2$ (where t is 1 to 2) where each $R^{14}$ is--.

Column 42, Line 37:
"of $C_4$-$C_{12}$cycloalkylalkyl is optionally substituted b one" should read, --of $C_4$-$C_{12}$cycloalkylalkyl is optionally substituted by one--.

Column 42, Line 45:
"-$R^{15}$-$N(R^{14})^2$," should read, -- -$R^{15}$-$N(R^{14})_2$,--.

Column 42, Line 48:
"-$R^{15}$-$S(O)_tOR^{19}$" should read, -- -$R^{15}$-$S(O)_tOR^{16}$--.

Column 43, Line 57:
"$C_4$-$C_{12}$heteroalkylalkyl" should read, --$C_4$-$C_{12}$cycloalkylalkyl--.

Column 45, Line 32:
"$C_1$-$C_1C_{12}$alkyl;" should read, --$C_1$-$C_{12}$alkyl;--.

Column 47, Lines 54-55:
"$N(R^{14})(S(O)_tR^{16}$)" should read, -- -$N(R^{14})(S(O)_tR^{16})$--.

Signed and Sealed this
Ninth Day of April, 2013

Teresa Stanek Rea
*Acting Director of the United States Patent and Trademark Office*

CERTIFICATE OF CORRECTION (continued)
U.S. Pat. No. 8,030,488 B2

Column 47, Line 60:
"haloC$_1$-C$_{12}$alkyl," should read, --C$_3$-C$_{12}$heterocyclyl,--.

Column 48, Line 15:
"and –R$^{15}$—S(O)$_t$N(R$^{14}$), (where t is 1 to 2) where each" should read, --and –R$^{15}$—S(O)$_t$N(R$^{14}$)$_2$, (where t is 1 to 2) where each--.

Column 48, Line 31:
"C$_1$-C$_2$alkyl," should read, --C$_1$-C$_{12}$alkyl,--.

Column 48, Lines 65-66:
"–R$^{15}$—C(O)OR$^{16}$, –R$^{15}$—C(O)OR$^{14}$, -R$^{15}$-C(O)N(R$^{14}$)$_2$" should read, -- –R$^{15}$—C(O)OR$^{14}$, -R$^{15}$-C(O)N(R$^{14}$)$_2$--.

Column 49, Line 17:
"each of C$_1$-C$_{12}$heteroaryl or the heteroaryl art of" should read, --each of C$_1$-C$_{12}$heteroaryl or the heteroaryl part of--.